United States Patent
Kantner

(10) Patent No.: US 8,114,386 B2
(45) Date of Patent: Feb. 14, 2012

(54) TOPICAL INSECT REPELLENT COMPOSITION AND METHOD OF APPLICATION

(75) Inventor: Steven S. Kantner, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 761 days.

(21) Appl. No.: 11/382,976

(22) Filed: May 12, 2006

(65) Prior Publication Data

US 2007/0264295 A1    Nov. 15, 2007

(51) Int. Cl.
*A61K 7/42* (2006.01)
(52) U.S. Cl. ...... 424/59; 424/60; 424/78.02; 424/78.08; 424/78.17; 424/400; 424/405
(58) Field of Classification Search .................. 424/59, 424/60, 78.02, 78.08, 78.17, 400, 405
See application file for complete search history.

(56) References Cited

U.S. PATENT DOCUMENTS

| | | | |
|---|---|---|---|
| 3,590,118 A | 6/1971 | Conrady et al. | |
| 3,873,725 A | 3/1975 | Skinner et al. | |
| 4,774,082 A | 9/1988 | Flashinski et al. | |
| 4,816,256 A | 3/1989 | Randen | |
| 5,001,156 A | 3/1991 | Philippe et al. | |
| 5,073,372 A | 12/1991 | Turner et al. | |
| 5,518,712 A | 5/1996 | Stewart | |
| 5,653,965 A * | 8/1997 | Narayanan et al. | 424/59 |
| 5,716,602 A | 2/1998 | Uick | |
| 5,997,887 A | 12/1999 | Ha et al. | |
| 6,180,127 B1 | 1/2001 | Calton et al. | |
| 6,258,857 B1 | 7/2001 | Iijima et al. | |
| 6,284,227 B1 | 9/2001 | Stewart | |
| 6,441,034 B1 | 8/2002 | Roy | |
| 6,605,643 B1 | 8/2003 | Ross | |
| 8,719,959 | 4/2004 | Gonzalez et al. | |
| 6,969,521 B1 | 11/2005 | Gonzalez et al. | |
| 6,984,391 B2 | 1/2006 | Fox et al. | |
| 2003/0129213 A1 | 7/2003 | Gonzalez et al. | |

OTHER PUBLICATIONS

Seo et al., "Biodegredation of the Insectide N,N-Diethyl-m-Toluamide by Fungi: Identification and Toxicity of Metabolites", 2005, Archives of Environmental Contamination and Toxicology, vol. 48, pp. 323-328.*

"Permethrin Repellents," [retrieved from the internet Jan. 24, 2006], URL <http://www.tickinfo.com/Permethrin.htm> Your Best Source for Learning About and Protecting Yourself from Ticks & Mosquitos, pp. 1-3.

"Repellents," [retrieved from the Internet Jan. 24, 2006], URL <http://www.travmed.com/trip_prep/insect_repellents.htm>, pp. 1-3.

* cited by examiner

*Primary Examiner* — Karlheinz R Skowronek
*Assistant Examiner* — Ali Soroush
(74) *Attorney, Agent, or Firm* — Robert H. Jordan; Lisa P. Fulton

(57) ABSTRACT

Stable, single phase, low VOC, topical insect repellent compositions containing a film-forming polymer, insect repellent, water miscible organic solvent, and water.

17 Claims, No Drawings

TOPICAL INSECT REPELLENT COMPOSITION AND METHOD OF APPLICATION

FIELD OF INVENTION

The present invention relates to a topical insect repellent composition and a method of applying insect repellent materials.

BACKGROUND

Insects such as mosquitoes and ticks are not merely a nuisance, but can carry debilitating and sometimes fatal diseases that they infect their host with. Chemicals that repel these insects when placed on skin have been known for years with several of them also showing acceptably low levels of skin irritation and toxicity to mammals. Known repellents which possess these attributes include sec-butyl 2-(2-hydroxyethyl)piperidine-1-carboxylate, p-menthane-3,8-diol, ethyl N-butyl-N-acetyl-3-aminopropionate, and N,N-diethyl-meta-toluamide (referred to herein as "DEET"), with the latter being the most widely used.

Although a repellent such as DEET is not readily soluble in water, perspiration or exposure to water can decrease its concentration on skin, leading to formation of areas without adequate levels for repellency. Many patents disclose means of improving the water and sweat resistance of insect repellents by delivering them in a matrix of water-insoluble materials, particularly polymers that also provide abrasion and "rub-off" resistance. U.S. Pat. No. 3,590,118 discloses the use of a terpolymer of (meth)acrylic acid, ethyl or methyl methacrylate, and a $C_1$ to $C_{10}$ acrylate. U.S. Pat. No. 4,774,082 discloses the use of a copolymer of maleic anhydride and 1-alkene where from 10 to 40 mole percent of the polymer is a $C_{18}$ to $C_{30}$ 1-alkene. U.S. Pat. No. 6,180,127 discloses the use of a copolymer of vinylpyrrolidone and a $C_4$ to $C_{30}$ 1-alkene. U.S. Pat. No. 4,816,256 discloses the use of a terpolymer of isooctyl acrylate, stearyl methacrylate, and acrylic acid with a solubility parameter of 6 to 10 $(cal/gm)^{1/2}$. Formulations containing these hydrophobic polymers are typically delivered from solutions containing high levels of lower alcohols such as ethanol or isopropanol that can cause irritation and drying of the skin.

Renewed focus has been placed on reduction of pollutants, particularly volatile organic compounds (referred to herein as "VOCs") that create air pollution problems. The State of California has led the effort to reduce the emission of these VOCs from consumer products, limiting the percentage that can be included in products for sale. For non-aerosol insect repellents, the California Air Resources Board recently considered restricting the VOC content to 30% or less. The most straightforward and economical way to attain such a low VOC level in a cosmetically acceptable insect repellent is to use water as the major solvent. However, many of the repellents as well as the polymers used to impart splash and sweat resistance are not soluble in aqueous or hydroalcoholic solutions. Delivery as an emulsion with the polymer dissolved in the oil phase repellent is possible as disclosed in U.S. Pat. Nos. 6,605,643, 5,518,712, and 5,716,602. However, such two phase emulsions present problems with long term and freeze thaw stability, have prolonged dry times, may not wet and spread well on skin, and often include water-soluble surfactants that detract from their splash and sweat resistance and may irritate the skin.

A need thus exists for a low VOC/high water content topical insect repellent composition that is stable and single phase, non-irritating to the skin, spreads well and dries quickly, and contains a film-forming polymer that provides improved sweat and splash resistance on drying.

SUMMARY OF INVENTION

This invention provides stable, low VOC, topical insect repellent compositions that provide improved sweat and splash resistance and also methods for applying such compositions.

Stable, low VOC, water-based compositions containing high levels of water-insoluble topical insect repellents are provided herein as single-phase solutions containing a film-forming polymer. The repellent and film-forming polymer are solubilized by partial neutralization with a base and addition of a low level of water miscible organic solvent. These compositions are stable, non-irritating to the skin, spread well and dry quickly on skin providing repellency with improved splash and sweat resistance. A surfactant or emulsifier is not required nor is it desirable as it will detract from the splash and sweat resistance provided by the film-forming polymer.

In one aspect, the present invention relates to insect repellent compositions that are useful in repelling insects from a host. The term "host" is used herein to refer to a human or other warm blooded mammal. In brief summary, a topical insect repellent composition of the invention comprises, based upon the total weight of the composition, a single-phase solution of:

a) an effective amount, e.g., from about 0.5 to about 8%, of a film forming methyl vinyl ether-maleic acid monobutyl or monoethyl ester copolymer comprising neutralized carboxylic acid groups, e.g., at 15% or greater;

b) an effective amount, e.g., from about 7.5 to about 35%, of an insect repellent selected from the group consisting of sec-butyl 2-(2-hydroxyethyl)piperidine-1-carboxylate, ethyl N-butyl-N-acetyl-3-aminopropionate, N,N-diethyl-meta-toluamide, p-menthane-3,8-diol and mixtures thereof, c) an effective amount, e.g., from about 1 to less than about 30%, of a water miscible organic solvent selected from the group consisting of ethanol, 1-propanol, isopropanol, and mixtures thereof, and d) an effective amount, e.g., from about 35 to about 60%, water.

It has been unexpectedly found that such compositions can be surfactant-free and still provide effective performance.

In another aspect, the invention provides a method of repelling insects from a host comprising topically applying to the skin of the host an effective amount of insect repellent composition as described herein and drying the applied composition in situ.

DETAILED DESCRIPTION OF ILLUSTRATIVE EMBODIMENTS

As used herein, all references to "percent" or "%" mean percent by weight unless otherwise indicated.

In brief summary, topical insect repellent compositions of the invention comprise, based upon the total weight of the composition, a single-phase surfactant-free solution of:

a) an effective amount, e.g., from about 0.5 to about 8%, of a film forming methyl vinyl ether-maleic acid monobutyl or monoethyl ester copolymer comprising neutralized carboxylic acid groups, e.g., at 15% or greater;

b) an effective amount, e.g., from about 7.5 to about 35%, of an insect repellent selected from the group consisting of sec-butyl 2-(2-hydroxyethyl)piperidine-1-carboxylate, ethyl N-butyl-N-acetyl-3-aminopropionate, N,N-diethyl-meta-toluamide, p-menthane-3,8-diol and mixtures thereof, c) an effective amount, e.g., from about 1 to less than about 30%, of a water miscible organic solvent selected from the group consisting of ethanol, 1-propanol, isopropanol, and mixtures thereof, and d) an effective amount, e.g., from about 35 to about 60%, water.

The inventive compositions are prepared as single-phase systems using skin-compatible insect repellents, carboxylic acid containing film-forming polymers, and neutralization agents for partial neutralization of the polymers, all dissolved in a water miscible solvent/water medium. Homogeneous compositions can be obtained by gentle mixing with a mechanical stirrer, e.g., for a period of one hour, depending upon the conditions and materials selected.

The carboxylic acid containing film-forming polymer is preferably a half-ester of alternating copolymers of methyl vinyl ether and maleic acid. Preferred half-esters include ethyl or butyl esters and mixtures thereof. The butyl ester is most preferred. Such polymers have variable and selective solubility in various media depending upon the alkanol used for esterification, the molecular weight of the copolymer, the presence of a water miscible cosolvent, and the extent to which the copolymer is neutralized and the type of neutralizing agent employed. These polymers may be readily obtained commercially. The butyl monoesters produce softer and more water-resistant films. Both the ethyl and butyl monoesters, if neutralized to a high degree, become completely soluble in aqueous solution, although films of ethyl monoester-based polymer become more water-sensitive when neutralized and this is accompanied by an increase in the degree of tack. Tack-free films are obtained by using the butyl monoester based polymer because, even with neutralization, such a polymer is inherently more resistant to water.

A balance is achieved between solubility of the polymer in the water miscible solvent, the amount of water and water miscible solvent, the level of insect repellent incorporated, and the level of neutralization of the polymer. It is desirable to have a low level of water miscible solvent to reduce pollution and satisfy governmental regulation. Generally less than about 30% of the composition is water miscible solvent, with lower alcohols being preferred. Ethanol, isopropanol, and 1-propanol, and mixtures thereof are specifically preferred lower alcohols with ethanol being most preferred. Generally at least about 10% of the composition is water miscible solvent with at least about 20% typically being preferred. Lower water miscible solvent content tends to reduce the solubility of the polymer and insect repellent in the composition and may lead to slower drying and poorer wetting.

The level of neutralization is chosen to keep the pH formulation in the neutral to slightly acidic region, generally in the range of pH about 5.0 to about 7.5. Thus generally at least about 15%, preferably at least about 20%, and most preferably at least about 25% of the carboxylic acid groups on the polymer are neutralized with higher levels allowing for good solubility of the polymer even in the presence of low alcohol or insect repellent.

The neutralization agents can be alkali metal hydroxides, e.g., sodium and potassium hydroxide, primary, secondary and tertiary amines, and alkanolamines, e.g., triisopropanolamine, aminomethylpropanediol, and aminomethylpropanol. The use of a neutralizing agent that has significant volatility will yield a less water sensitive polymer film on drying. The volatile neutralizing agent of the composition is any alkaline compound sufficiently volatile to be substantially eliminated within an hour or so. The preferred alkali from the standpoint of economy and ease of handling is ammonia in the form of ammonium hydroxide. Others are also suitable including the mono (lower alkyl) amines such as monomethylamine, monoethylamine, and monoisopropylamine, and heterocyclic compounds such as morpholine. They may be employed singly or in admixture.

The amount of film-forming polymer component varies depending upon the solubility of the particular resin in the vehicle employed, such as water or an alcohol-water system, and the amount of insect repellent present. Typically the amount of film-forming polymer present in the composition is from about 0.5% to about 8.0%, preferably about 2.0% to about 6.0% based on the total composition. Typically the weight ratio of insect repellent to film-forming polymer is at least about 2:1 and less than about 20:1, preferably at least about 3:1 and less than about 10:1, and most preferably at least about 4:1 and less than about 8:1. Compositions containing too little film-forming polymer will tend to provide insufficient sweat and splash resistance on the host. Compositions containing excessive quantities of film-forming polymer will tend to result in thicker, potentially gooey or distasteful coatings on the host.

The insect repellent is preferably selected from the group consisting of N,N-diethyl-m-toluamide (also known as "DEET" or N,N-diethyl 3-methylbenzamide), p-menthane-3,8-diol, sec-butyl 2-(2-hydroxyethyl)-1-piperidinecarboxylate, and ethyl 3-N-butyl-N-acetyl-3-aminopropionate, and mixtures thereof. Other compounds such as dipropyl 2,5-pyridinedicarboxylate and N-octyl bicycloheptene dicarboximide can be added to broaden the spectrum of the repellency or enhance the effectiveness of the repellent. If DEET is used, the DEET content of the composition is preferably in the range of about 7.5% to about 35%, more preferably in the range of about 10% to about 30% and most preferably in the range of about 15% to about 25%. DEET contents in these ranges give effective repellency for several hours while satisfying global regulatory requirements. For example, in some embodiments of the invention, the composition will comprise only up to about 20% DEET, thus conforming to maximum loading levels of DEET suggested by some while providing effective insect repellency.

The insect repellent compositions of the invention may be formulated in a variety of ways. For example, the insect repellent, a portion of the water miscible solvent, and water may be charged into a vessel in any order followed by the neutralizing agent and then the polymer predissolved in concentrated form in the remainder of the water miscible solvent. Alternatively, the polymer can be dissolved in the water miscible solvent or insect repellent or a blend of the two and the resulting solution diluted with water then neutralized, or diluted with water to which the neutralizing agent has already been added. Other methods of forming these compositions are also useful.

As used herein, the term "surfactant-free" means that the composition contains no more than about 1%, preferably less than about 0.5%, of surfactant. In some embodiments, the composition will be substantially free of surfactant. It has been surprisingly found that stable solutions can be obtained without using surfactants or emulsifiers.

The delivery of this insect repellent composition to the skin or clothing of the host can be done in a variety of ways. The composition can be poured on, sprayed on with a pump spray, wiped on from a pre-saturated towelette, e.g., fashioned from paper or a woven or non-woven fabric, or delivered from a pressurized aerosol. Thickening with a suitable thickening agent provides a gel or ointment.

Other therapeutically or cosmetically active ingredients may be incorporated if desired. For example, fragrances, perfumes, essential oils, sunscreening agents, sunblocking agents, vitamins, plant extracts, silicones, anti-inflammatory agents, anti-oxidants, humectants, emollients, and antibacterial agents can add utility and value to the compositions of the present invention.

While the invention has been described with particular reference to certain embodiments thereof, it will be understood that changes and modifications may be made which are within the skill of the art.

EXAMPLES

The invention will be further explained by the following illustrative examples which are intended to be non-limiting. Unless otherwise indicated, all amounts are expressed in parts by weight.

Preparation of Test Formulations 19.34 grams of 98.25% pure N,N-diethyl toluamide (DEET from Morflex Incorporated, Greensboro, N.C.) was charged into a clean glass jar. 26.11 grams of 190 proof SDA 40B denatured alcohol (Equistar Chemicals, Tuscola, Ill.) and 46.03 grams deionized water were added and mixed followed by slow addition of 0.32 grams concentrated ammonium hydroxide (J.T. Baker, Phillipsburg, N.J.). The mixture was stirred yielding a hazy solution. 8.0 grams of Gantrez A-425 from International Specialty Products Corporation, Wayne, N.J. (50% solids poly(methyl vinyl ether-alt-maleic anhydride monobutyl ester) in ethanol) was added and the mixture stirred until a homogeneous solution was obtained. 0.20 grams of SZ 4820 fragrance from J & E Sozio Inc., Edison, N.J. was mixed in to yield the Example formulation.

A Comparative Example formulation was prepared from 19.34 grams of DEET, 30.31 grams of 190 proof SDA 40B denatured alcohol, 50.15 grams of deionized water, and 0.20 grams of SZ-4820 fragrance.

Determination of In-Vivo Substantivity

The in-vivo substantivity of a composition was determined after water exposure by quantifying the amount of applied active agent still present on a test site. The method consists of applying an active agent to a participant's forearm, letting it dry, challenging the test site in a water bath for thirty seconds, and then extracting the site. The extracted solutions are analyzed on a gas chromatograph to determine the amount of active agent present on said site. This can be compared to the theoretical amount applied and the percent retention calculated—the higher the percent retention, the more substantive the composition.

The steps used in carrying out the substantivity test are as follows:

1) The outside portion of the subject's lower arm (below the elbow), is washed with Ivory soap by passing lathered hands up and down the arm five times. The soap is rinsed with tap water and the arm is patted dry with a clean cloth or paper towel.
2) The subject sits in a chair with his/her arm resting on a table. The palm of the hand faces upwardly and the elbow is bent at a 90° angle.
3) A 6×12 cm template cut from the adhesive portion of Post-it® Self Stick Easel Pad is adhered to the broadest portion of the subject's inner forearm.
4) A minimal grease barrier (Apiezon N, Apiezon Products Ltd., London) ⅛ inch wide is applied around the margin of the template. This grease barrier prevents spreading of the test composition.
5) A 0.20 mL aliquot of the test composition is applied to the lower half of the test site and spread evenly and thoroughly over the 6×6 cm area with a needleless syringe. Another 0.20 mL aliquot of the same test composition is applied in the same manner to the upper half of the 6×12 cm area.
6) The control composition is applied to the other arm in the same manner.
7) The test composition is allowed to equilibrate on the test site for 5 minutes. During this time, a water bath is prepared using 35° C. (95° F.) tap water.
8) The arm is placed in a horizontal position in the bath with the volar portion of the arm facing down. The arm is slowly moved from one side of the bath to the other three times in 30 seconds.
9) The arm is removed from the water bath and the area around the test site is towel-dried. A stream of compressed air is used to gently blow water drops from the test site.
10) The test site is extracted immediately at two locations with the subject's arm in the same position as in Step 2. One end of a hollow glass cylinder 25 mm long and having an inside diameter of 41 mm, is lubricated with a thin layer of Apiezon N grease to prevent solvent leakage. This end of the cylinder is pressed onto the lower portion of the test site by the subject. Ten (10.0) mL of isopropanol (IPA) is poured into the cylinder on the test site. The IPA is agitated by using a 2 mL disposable plastic pipette to withdraw and discharge the solvent in the glass cylinder. The force of the discharged solvent is directed at different locations each time. After eleven (11) such cycles, the IPA is removed completely and placed in a container that is tightly capped. The glass cylinder is carefully removed so as not to allow any residual solvent to run into the other half of the test site. The extracted side is wiped dry with a tissue and then the upper site extracted with fresh IPA as above.
11) The water bath is emptied and wiped with a paper towel after each test.
12) This procedure is repeated with the other arm, using the Comparative formulation.
13) The test sites are wiped with a isodecane saturated paper towel to remove the Apiezon grease barrier and any residual DEET. The arms are then washed with soap and water and dried.

A Hewlett Packard™ 5890A gas chromatograph with a flame ionization detector, equipped with an HP 3396A Integrator, an HP 7673 Automatic Sampler and a J&W DB-5 column, 30 M×0.25 mm ID×0.5 micron film thickness was used to analyze the samples. The following procedure is employed.

1) Two DEET standard samples containing 0.0364% and 0.113% DEET in IPA were generated using an analytical balance.
2) The DEET standards were analyzed on the gas chromatograph using conditions that give reasonable retention times for DEET. This will vary depending on column used, temperatures used, flow rates, etc.
3) The extraction samples obtained in Step 10 above were also evaluated on the chromatograph. The chromatograph will yield the integrated response of the DEET in the extraction samples. From this, the percent DEET retention on the participants was calculated.

Calculations

The theoretical applied amount of DEET for both the Example and Comparative Example was the volume of sample (2×0.20 mL) times its density (0.96 g/mL) times its percent in solution (19%) equaling 73.0 mg. This was spread over a 6×12=72 cm area—in other words theoretically 1 mg DEET per $cm^2$ was applied. Using the 4.1 cm diameter cylinder, only $2\times\pi(2.05)^2=26.4$ cm$^2$ were extracted with 20 mL ($\times0.785$ g/mL density) IPA, so the maximum contained (100% retention) is 26.4 mg in 15.7 g IPA or 0.168%.

The standards thus represent 0.0364/0.168=21.7% retention and 0.113/0.168=67.3% retention. By dividing these percentages by the response obtained, a % retention per unit respeonse for the set injection volume was obtained as shown in Table 1.

TABLE 1

| Sample | Injection | Response | mg DEET/g | % Recovery | % Recovery/Response |
|--------|-----------|----------|-----------|------------|---------------------|
| A | 1 | 170925 | 0.363 | 21.7 | 0.000126956 |
|   | 2 | 168993 | 0.363 | 21.7 | 0.000128408 |
|   | 3 | 167155 | 0.363 | 21.7 | 0.00012982 |
|   | 4 | 169335 | 0.363 | 21.7 | 0.000128148 |
| B | 1 | 436598 | 1.1173 | 67.3 | 0.000154146 |
|   | 2 | 434896 | 1.1173 | 67.3 | 0.00015475 |
|   | 3 | 441486 | 1.1173 | 67.3 | 0.00015244 |
|   | 4 | 440091 | 1.1173 | 67.3 | 0.000152923 |
|   |   |        |        | Average | 0.000140949 |

Multiplying the response for the extractions from step 10 by this number then gives % retention after water challenge. Results are shown in Table 2 and demonstrate that having the polymer present increases the retention 17% in one case and 32% in the other.

TABLE 2

| Subject | Arm | Formula | Average % Retention | Ratio of Example to Comparative |
|---------|-----|---------|---------------------|--------------------------------|
| X | R | Comparative | 41.14 | |
| X | L | Example | 48.13 | 1.17 |
| Y | L | Comparative | 51.32 | |
| Y | R | Example | 67.61 | 1.32 |

Various modifications and alterations of this invention will become apparent to those skilled in the art without departing from the scope and spirit of this invention.

What is claimed is:

1. A single phase, surfactant-free, topical insect repellent composition comprising:
   a) an effective amount of one or more film-forming methyl vinyl ether-maleic acid monobutyl or monoethyl ester copolymers comprising neutralized carboxylic acid groups;
   b) an effective amount of one or more insect repellents selected from the group consisting of sec-butyl 2-(2-hydroxyethyl)piperidine-1-carboxylate, ethyl N-butyl-N-acetyl-3-aminopropionate, N,N-diethyl-meta-toluamide, p-menthane-3,8-diol, and mixtures thereof;
   c) an effective amount of one or more water miscible organic solvents selected from the group consisting of ethanol, 1-propanol, isopropanol, and mixtures thereof; and
   d) water.

2. The composition of claim 1 wherein said composition comprises from about 0.5% to about 8% of said film-forming polymer.

3. The composition of claim 1 wherein said composition comprises from about 2% to about 6% of said film-forming copolymer.

4. The composition of claim 1 wherein at least 15% of the carboxylic acid groups are neutralized.

5. The composition of claim 1 wherein at least 20% of the carboxylic acid groups are neutralized.

6. A composition of claim 1 wherein at least 25% of the carboxylic acid groups are neutralized.

7. The composition of claim 1 wherein said composition comprises from about 7.5% to about 35% of said insect repellent.

8. The composition of claim 1 wherein said composition comprises from about 10% to about 30% of said insect repellent.

9. The composition of claim 1 wherein said composition comprises from about 15% to about 25% of said insect repellent.

10. The composition of claim 1 wherein said composition comprises up to about 20% of N,N-diethyl-meta-toluamide.

11. The composition of claim 1 wherein said composition comprises from about 1% up to less than about 30% of said water miscible solvent.

12. The composition of claim 1 wherein said composition comprises from about 10% to about 20% of said water miscible solvent.

13. The composition of claim 1 wherein said composition comprises from about 35 to about 60% water.

14. The composition of claim 1 further comprising one or more therapeutically or cosmetically active ingredients selected from the group consisting of fragrances, perfumes, essential oils, sunscreening agents, sunblocking agents, vitamins, plant extracts, silicones, anti-inflammatory agents, anti-oxidants, humectants, emollients, and antibacterial agents.

15. The composition of claim 1 having a pH in the range of about 5.0 to about 7.5.

16. A method of protecting a host from insect bites comprising the step of topically applying to the skin of the host an amount which is effective to protect the skin from said bites of the composition of claim 1 and drying.

17. The method of claim 16 wherein said applying comprises pouring, spraying, pumping, or wiping with towelette moistened with said composition.

* * * * *

UNITED STATES PATENT AND TRADEMARK OFFICE
CERTIFICATE OF CORRECTION

PATENT NO. : 8,114,386 B2
APPLICATION NO. : 11/382976
DATED : February 14, 2012
INVENTOR(S) : Steven Shepard Kantner Page 1 of 1

It is certified that error appears in the above-identified patent and that said Letters Patent is hereby corrected as shown below:

On the Title page,
Item [56], References Cited, under US PATENT DOCUMENTS, delete "8,719,959" and insert -- 6,719,959 --, therefor.
Item [56], References Cited, under OTHER PUBLICATIONS, Seo et al., delete ""Biodegredation" and insert -- "Biodegradation --, therefor.
Item [56], References Cited, under OTHER PUBLICATIONS, Seo et al., delete "Insectide" and insert -- Insecticide --, therefor.
Item [56], References Cited, under OTHER PUBLICATIONS, 2$^{nd}$ reference, delete "Mosquitos," and insert -- Mosquitoes, --, therefor.

In the Specification
Column 2,
Line 38, delete "thereof," and insert -- thereof; --, therefor.
Line 42, delete "thereof," and insert -- thereof; --, therefor.

Column 3,
Line 3, delete "thereof," and insert -- thereof; --, therefor.
Line 7, delete "thereof," and insert -- thereof; --, therefor.

Column 6,
Line 66, delete "cm" and insert -- $cm^2$ --, therefor.

Column 7,
Line 7, delete "respeonse" and insert -- response --, therefor.

Signed and Sealed this
Twenty-fourth Day of September, 2013

Teresa Stanek Rea
*Deputy Director of the United States Patent and Trademark Office*